United States Patent [19]

Terai et al.

[11] Patent Number: 4,968,535
[45] Date of Patent: Nov. 6, 1990

[54] METHOD OF PRODUCING GRADIENT GEL MEDIUM MEMBRANE FOR ELECTROPHORESIS

[75] Inventors: Fumitaka Terai; Kimio Yukawa; Mineo Suyefuji; Hiroki Saito; Shigeru Yamaguchi, all of Kanagawa, Japan

[73] Assignee: Fuji Photo Film Co., Ltd., Kanagawa, Japan

[21] Appl. No.: 199,726

[22] Filed: May 27, 1988

[30] Foreign Application Priority Data

May 29, 1987 [JP] Japan ............................ 62-131502
Jun. 16, 1987 [JP] Japan ............................ 62-147828

[51] Int. Cl.⁵ .................................................. B05D 3/12
[52] U.S. Cl. ............................... 427/358; 204/182.8; 204/299 EC; 427/420
[58] Field of Search ......... 204/182.8, 299 R, 299 EC; 252/315.1; 264/171, 207, 216, 217; 427/356, 358, 420, 389.9; 118/410, 411; 425/131.1, 461

[56] References Cited

U.S. PATENT DOCUMENTS

| | | | |
|---|---|---|---|
| 3,529,050 | 9/1970 | Smith | 425/131.1 |
| 4,623,501 | 11/1986 | Ishizaki | 264/171 |
| 4,649,026 | 3/1987 | Postle et al. | 427/2 X |
| 4,657,656 | 4/1987 | Ogawa | 204/299 R |
| 4,699,680 | 10/1987 | Shiraishi et al. | 156/242 |

FOREIGN PATENT DOCUMENTS

| | | |
|---|---|---|
| 0116404 | 1/1984 | European Pat. Off. |
| 0159694 | 4/1985 | European Pat. Off. |
| 0169397 | 6/1985 | European Pat. Off. |
| 61-39617 | 4/1986 | Japan |
| 61-22903 | 6/1986 | Japan |

Primary Examiner—Michael Lusignan
Attorney, Agent, or Firm—Sughrue, Mion, Zinn, Macpeak & Seas

[57] ABSTRACT

A method for producing gradient gel medium membrane for electrophoresis in which a monomer solution having a continuous concentration gradient and a polymerizing reaction initiator solution are supplied to a coating head as a gel forming solution for electrophoresis while mixing the monomer solution and the polymerizing reaction initiator solution with each other so as to coat a moving web with the gel forming solution. The coating liquid is supplied onto a moving web through the coating head in such a manner so that the flow of the coating liquid extends continuously in the direction of width and is continuously reduced in the direction of thickness along the coating head from its supply inlet to its slot opening.

4 Claims, 5 Drawing Sheets

METHOD OF PRODUCING GRADIENT GEL MEDIUM MEMBRANE FOR ELECTROPHORESIS

BACKGROUND OF THE INVENTION

The present invention relates to a method for producing gradient gel medium membrane for electrophoresis for determining the base sequence of DNA or DNA partially decomposed material or for separating/analyzing protein, particularly protein having a wide range of molecular-weight distribution, such as protein in urine.

Conventionally, in a plane electrophoretic method, high-molecular concentration gradient gel of acrylamide having no self-supporting property has been obtained by forming gel in layers having concentrations different from each other and stacked on one support or between two supports in the electrophoretic direction. Such a gradient gel has been used as a membranous material.

In the method in which gel is formed on a support when it is to be used, however, there has been a disadvantage in that the gel can sometimes be broken or damaged by dropping a material other than a sample onto the gel, when the gel is being formed on the support, when the gel is set in an electrophoretic tank, when the gel is in a state of preservation, or when the gel is added with a sample to be analyzed, and therefore close attention and much skill are required in operation.

In a vertical electrophoretic method in which gel is formed in a mold formed by two glass plates or the like, and electrophoretic analysis is performed while holding the mold vertically, on the other hand, there has been a disadvantage in that it is difficult to make the mold uniform in thickness, and a high degree of skill is required in operation to pour a gel forming solution into a narrow mold before the gel forming solution has gelled.

Particularly, in an operation for determining the base sequence of DNA, it is desirable to form an elongated sheet of gel so that pieces of DNA, as many as possible in number, can be analyzed using one sheet of gel. Difficulties in the production and handling of such an elongated sheet of gel, however, have been encountered. Further, since glass plates are used, there has been a disadvantage in that the glass plates are apt to be broken.

Recently, for industrially producing a gradient gel material for electrophoresis, there has been disclosed a method for producing gradient gel for electrophoresis including the steps of: preparing an aqueous solution or a water dispersion liquid of a mixture of acrylamide monomers and a cross-linking agent; adding a free radial generating material for initiating polymerization of the monomers by the absorption of light irradiation on the solution; forming the solution into the shape of a desired gel product; and adjusting the period of time of light irradiation on the monomer solution so as to change the porosity of the gel when the formed solution is subject to irradiation with light so as to cause polymerization and cross-linking in the monomer solution or the monomer dispersing liquid (see European Pat. No. 0169397A).

There have been further disclosed a method of producing gradient gel for electrophoresis having a concentration gradient of a polymer in the electrophoretic direction including the steps of: supplying two kinds of aqueous solutions differing in concentration from each other, each containing monomers, a cross-linking agent and a polymerization initiator, into a forming device while mixing the aqueous solutions with the mixing ratio therebetween gradually changed; and completing polymerization of the monomers with the cross-linking agent in the forming device; etc. (Japanese Pat. Publication Nos. 61-22903 and 61-39617).

Figure 1:
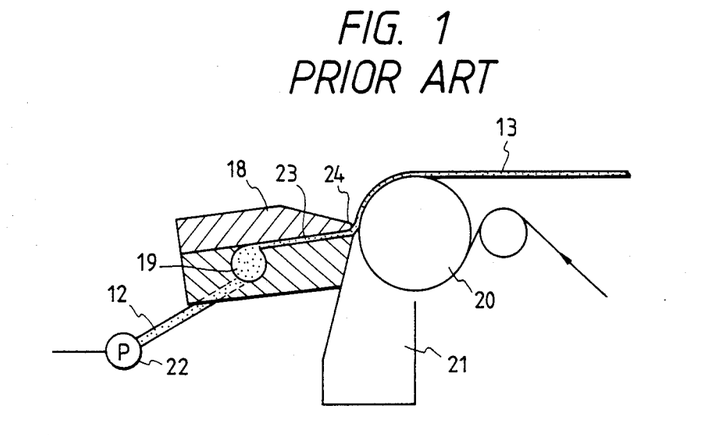
FIG. 1 is a side sectional view showing a conventional coating head.

For coating a continuously moving web with a gel forming solution for use for electrophoresis, a general coating head such as shown in FIG. 1 has been used. That is, the electrophoresis gel forming solution used as a coating liquid 12 is supplied in a pressurized state to a cavity 19 in a coating head 18 by a metering pump 22. The cavity 19 is employed as a liquid pool for supplying the coating liquid 12 to a slot 23 communicated with a slot opening 24 and extending over the coating width. The coating liquid 12 enters the slot 23 from the cavity 19, and is applied onto a web 13 on a coating roller 20 from the slot opening 24. In order to stabilize the coating process, a differential pressure chamber 21 is used so as to provide back pressure behind the coating bead.

The former method, however, has problems in that the cost is high because of the required light irradiation equipment and poor productivity, the resolution is low because of increased thickness of the gel, and it is impossible to obtain gradient gel having stability and reproducibility because the reaction initiator causes polymerizing and cross-linking reactions in the presence of light even after completion of production. The latter producing method, on the other hand, has problems in that the productivity is poor because it is a batch-type system, and it is difficult to uniformly branch a gel forming solution for electrophoresis when it is poured into forming devices, so that it is impossible to obtain gradient gel with reproducibility.

Further, products coated using the conventional coating head have problems in that the transverse film thickness is insufficient in uniformity, and in that foreign matter is generated during running over long periods, making it necessary to overhaul and clean the coating head.

SUMMARY OF THE INVENTION

It is therefore an object of the present invention to overcome the foregoing problems in the prior art.

It is another object of the present invention to provide a method for producing gradient gel medium membrane for electrophoresis in which gradient gel medium membrane for electrophoresis having a coating film thickness which is uniform over the whole coating width and which has a concentration gradient continuous in the moving direction of a web can be produced with high productivity, with improved stability, with good reproducibility, and without generation of any foreign matter.

The above objects of the present invention can be achieved by a method for producing gradient gel medium membrane for electrophoresis in which a monomer solution having a continuous concentration gradient and a polymerizing reaction initiator solution are supplied to a coating head as a gel forming solution for electrophoresis while mixing the monomer solution and the polymerizing reaction initiator solution with each other so as to coat a moving web with the gel forming solution, the method comprising the step of supplying the coating liquid onto the moving web through the coating head in a manner such that the flow of the coating liquid extends continuously in the direction of width but is continuously reduced in the direction of thickness along the coating head from its supply inlet to its slot opening.

Moreover, in the above-mentioned method for producing gradient gel medium membrane for electrophoresis, if the flow-rate ratio is changed to make the concentration gradually change from low to high and then from high to low, the changeover length of the coating liquid for each product unit length of the web can be shortened so that the production cost can be reduced and the reproducibility can be further improved.

The monomer solution having a continuous concentration gradient used in the practice of the present invention is prepared from high and low concentration monomer solutions supplied at respective flow rates, the ratio of which is continuously changed. It is preferable to select the rate of change of the concentration of the monomer solution within a range of from 3 to 35 W/V%.

Mixing according to the present invention may be carried out by a mixer in an ordinary tank; however, it is preferable to prepare the monomer solution using a static mixer.

The term "static mixer" as used herein means a mixer in which an agitating operation is generated by movement of fluids themselves when the fluids are passed through the mixer. Examples of such a mixer include tubular mixers composed of spiral tubes, right and left tubes spiraling alternately, propeller-shaped tubes with baffle boards, etc.

The gel forming solution for electrophoresis according to the present invention may be any kind of gel forming solution so long as it can form a medium membrane for electrophoresis. Typical examples of the gel forming solution include raw material solutions for acrylamide and agarose.

The coating of the electrophoresis gel forming solution according to the present invention may be carried out using a coating technique such as slide bead coating, extrusion coating, hopper coating, curtain coating, or the like. The thickness of the coating of the medium membrane is selected in accordance with the purpose of separation. Generally, the thickness should be in a range from 50 $\mu$m to about 1.0 mm, preferably, from about 200 $\mu$m to about 0.5 mm. In the case of porous film or filter paper, the thickness ranges from 70 $\mu$m to about 1.0 mm.

The moving web according to the present invention may be formed of any type of material so long as it is formed into a sheet having good flatness, is nonconductive, and substantially water-impermeable. Polyester such as polyethylene terephthalate, polycarbonate of bisphenol A or the like, a vinyl polymer such as polymethyl methacrylate, polyethylene, polystyrene, polyvinyl chloride or the like, polyamide such as nylon or the like, or a copolymer of those materials (for example, a vinylidene chloride copolymer or a vinyl chloride copolymer) is preferably used.

Supplying the coating liquid onto the moving web through the coating head in a manner so that the flow of the coating liquid extends continuously in the direction of width and continuously reduced in the direction of thickness along the coating head from its supplying inlet to its slot opening prevents vortices or stagnation from occurring within the flow (1) by making the edge lines of the coating liquid flow path from the supplying inlet to the slot opening continuously change not steeply but gently, (2) by reducing the thickness of the flow correspondingly when the width of the flow is increased, (3) by restricting the angles of extension and reduction of the flow, and the like. As a result, according to the present invention, the cavity used in the conventional coating head in unnecessary.

In the method and apparatus for producing gradient gel medium membrane for electrophoresis according to the present invention, an anion surfactant may be contained as a modifier in the medium layer for electrophoresis when the medium material for electrophoresis is used mainly for analysis of protein or conjugated protein, for example, lipoprotein, glycoprotein, or the like. When a sample to be analyzed is protein or conjugated protein, for example, lipoprotein, glycoprotein, or the like, it is preferable or indispensable in many cases to employ an anion surfactant. It is a matter of course that no anion surfactant is contained in the gel medium layer in some cases. For example, a gel medium layer containing no anion surfactant can be used for hereditary disease diagnosis performed on the basis of DNA fragment analysis or for DNA sequence analysis utilizing restriction enzyme decomposition.

It is possible to efficiently perform separation of protein or conjugated protein and to measure the molecular weight thereof by supplying an anion surfactant in the medium layer for electrophoresis.

As the anion surfactant, for example, alkyl sulfate may be used. It is preferable to use alkyl sulfate having a long chained alkyl radical of 10 or more carbon atoms. As the cation for forming salt, alkali metal ions such as sodium ions, potassium ions, lithium ions, or the like, are generally used. Of those ions, sodium ions may be used easily. Of the alkyl sulfates, it is preferable to use dodecyl sulfate, for example, sodium dodecyl sulfate, potassium dodecyl sulfate, lithium dodecyl sulfate, or the like. Of those dodecyl sulfates, sodium dodecyl sulfate (SDS) is most preferable. Use of SDS in the gel medium layer according to the present invention makes it possible to efficiently separate protein or conjugated protein and to measure the molecular weight thereof.

The content of the anion surfactant acting as the denaturant should range from about 0.05 W/V % to about 2.0 W/V %, preferably, from about 0.1 W/V % to about 1.5 W/V %. In such case, the thickness of coating of the medium membrane is selected in accordance with the purpose of separation. Generally, the thickness ranges from 50 $\mu$m to about 2.0 mm, preferably, from about 100 $\mu$m to about 1.0 mm.

BRIEF DESCRIPTION OF THE DRAWINGS

The above objects, features and advantages of the present invention will be apparent from the following detailed description taken in conjunction with the accompanying drawings, in which.

DESCRIPTION OF THE PREFERRED EMBODIMENTS

Figure 2:
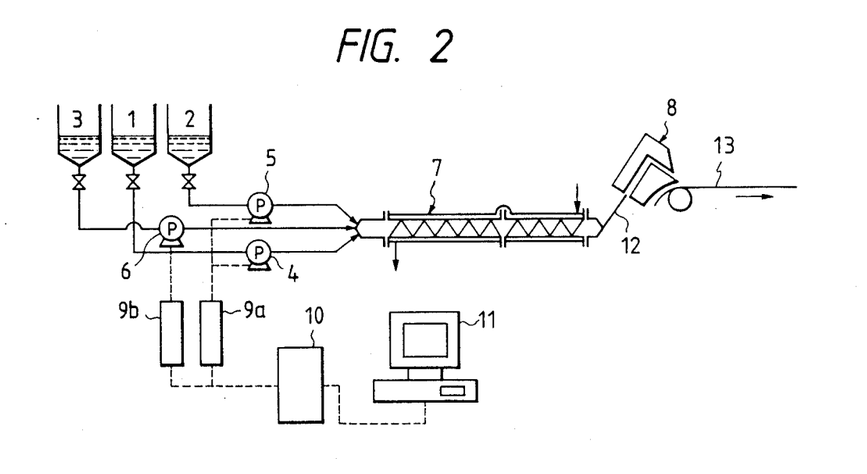
FIG. 2 is a diagram for explaining the process of the method for producing a gel forming solution for electrophoresis according to the present invention.

FIG. 2 is a diagram for explaining an embodiment of a method for producing gradient gel medium membrane for electrophoresis according to the present invention.

A low concentration monomer solution 1, a high concentration monomer solution 2, and a polymerizing reaction initiator solution 3 are mixed with each other while being agitated in a static mixer 7 to thereby prepare a gel forming solution 12 for electrophoresis.

Figure 3A:
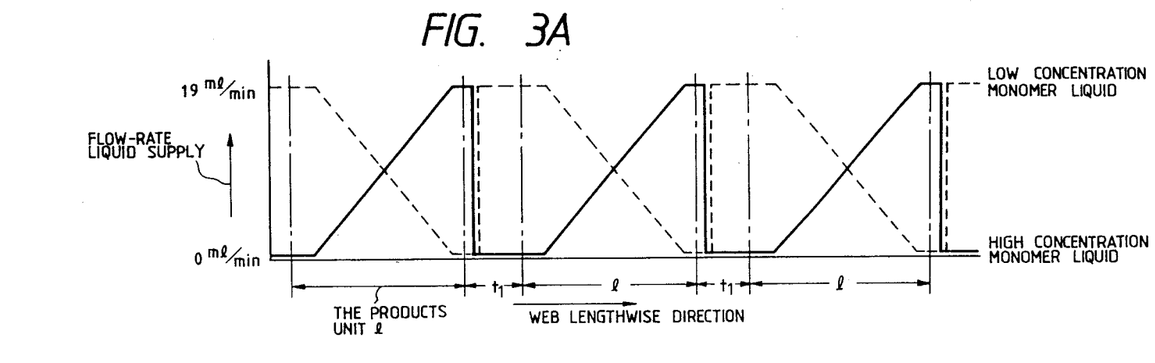
FIG. 3A is a diagram for explaining the concentration gradient of the gel forming solution for electrophoresis according to the present invention.

FIG. 3A is a diagram for explaining the relation of the flow-rate ratio between the high and low concentration monomer solutions according to the present invention. The continuous change of the flow-rate ratio is such that at initiation the high concentration monomer solution 2 and the low concentration monomer solution 1 are supplied at flow rates of 0 ml/min and 19 ml/min respectively. Then, the respective flow rates of the high concentration monomer solution 2 and the low concentration monomer solution 1 are continuously changed in a manner as shown by a solid line and a dotted line, respectively, under the condition that the sum of the flow rates is held constant at 19 ml/min. In the drawing, l represents the product unit length of the gradient gel medium membrane for electrophoresis. At the termination of a product unit length l along the web, the respective flow rates of the high and low concentration monomer solutions 2 and 1 are 19 ml/min and 0 ml/min, so that the membrane component at that time has a high concentration. In order to repeat such a change of flow-rate ratio, flow-rate gradient liquid supply pumps 4 and 5 are controlled by a controller 9a through a computer linkage adapter 10 in accordance with instructions from a computer 11 as shown in FIG. 2.

The polymerizing reaction initiator solution 3, on the other hand, is supplied at a predetermined rate to the static mixer 7 through a metering pump 6 controlled by a controller 9b. The low concentration monomer solution 1, the high concentration monomer solution 2, and the polymerizing reaction initiator solution 3 are agitated and mixed with each other in the static mixer 7 so that a gel forming solution 12 for electrophoresis is prepared. The gel forming solution for electrophoresis 12 is supplied to a coating head 8 so as to be applied onto a web 13.

Figure 3B:
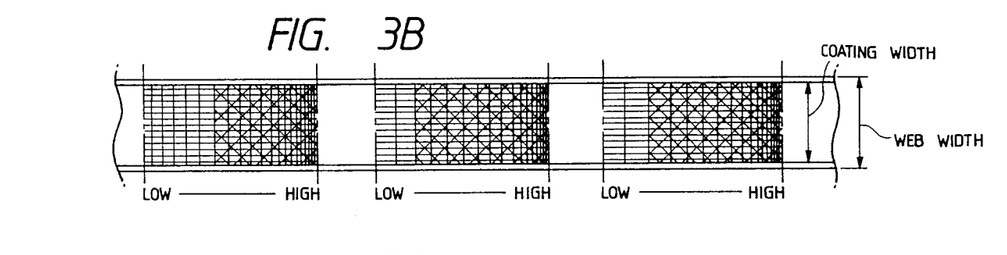
FIGS. 3B and 3C are plan and side views showing the coating film of the electrophoresis gel forming solution.
Figure 3C:
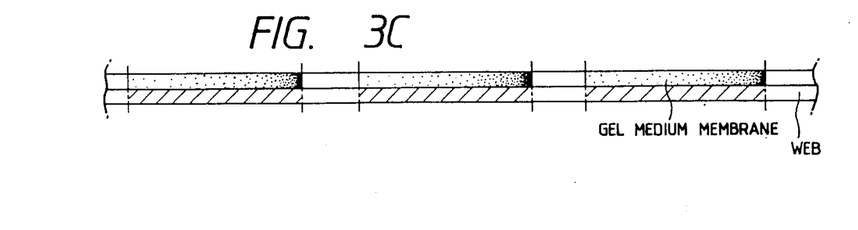

FIG. 3B is a plan showing the gradient gel medium membrane for electrophoresis formed by the concentration ratio of FIG. 3A, and FIG. 3C is a sectional view of FIG. 3B.

A gap $t_1$ between two adjacent product unit lengths l in FIG. 3A is punched as a sample pouring inlet portion where a sample pouring inlet is to be formed by a cover sheet or the like.

Figure 4A:
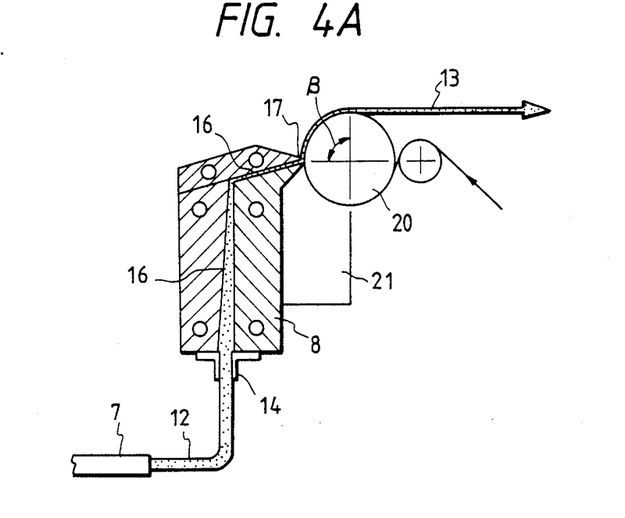
FIG. 4A and 4B are side sectional views showing a coating head according to the present.
Figure 4B:
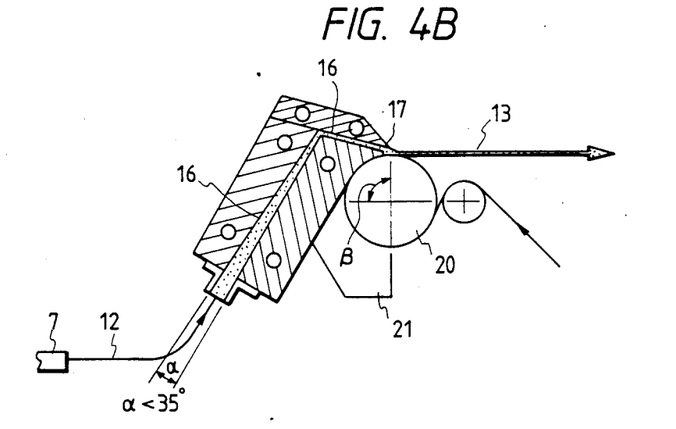

FIGS. 4A and 4B are side sectional views showing an embodiment of the coating head according to the present invention. The electrophoresis gel forming solution 12, which is a coating liquid supplied from the static mixer 7, is received by a coating head 8 at its supply inlet 14, and led to a slot opening 17 through a slot 16 so as to be applied onto the web 13 disposed on a coating roller 20.

FIG. 4B differs from FIG. 4A only in the position of the coating head 8 on the coating roller 20 on which the coating liquid 12 is applied onto the web 13. Accordingly, either coating head 8 shown in FIGS. 4A or 4B may be used.

According to the present invention, it is necessary to supply the coating liquid 12 from the supply inlet 14 into the slot 16 while continuously increasing the width and reducing the thickness of the supply of the coating liquid 12, with relatively gentle angles of extension in width and reduction in thickness. Accordingly, it is necessary to make the slot 16 of the coating head 8 longer than that of the conventional head, and therefore the position of the coating head 8 relative to the coating roller 20 is set as shown in FIGS. 4A and 4B.

Figure 5:
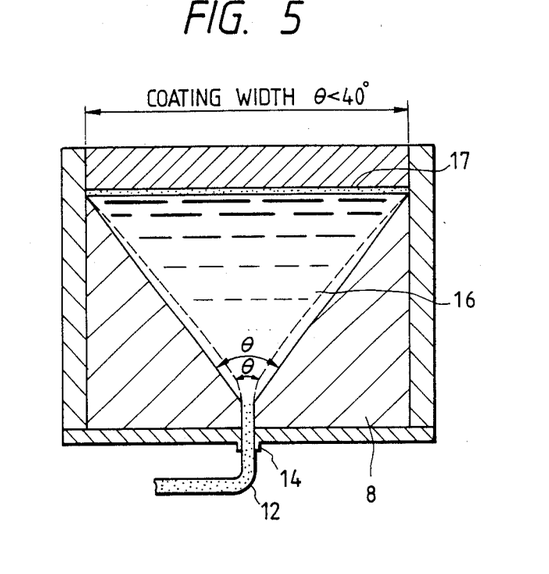
FIG. 5 is a front sectional view of FIG. 4.
Figure 6:
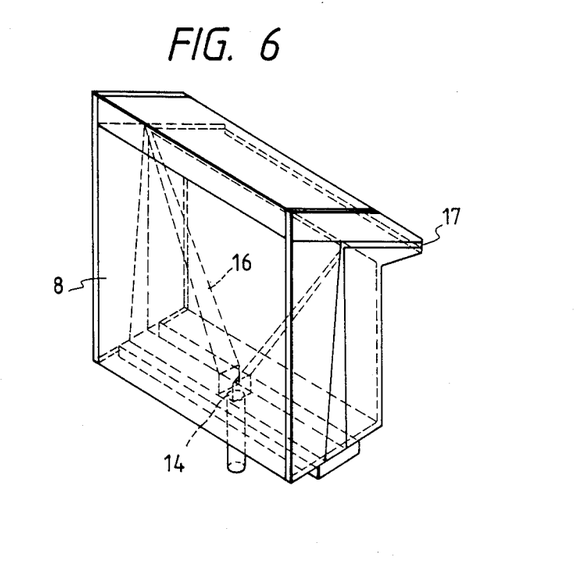
FIG. 6 is a perspective view of FIG. 5.

In FIG. 4B, it is preferable to select the angle $\alpha$ of reduction in width to be $\alpha \leq 0.35$. FIG. 5 is a sectional view showing the coating head 8 of FIGS. 4A and 4B when viewed from the front, and FIG. 6 is a perspective view of the same coating head 8. FIG. 5 shows the state where the slot 16 extends continuously in the direction of width from the coating liquid supplying inlet 14 of the coating head 8 to the slot opening 17. Although the slot 16 is ideally extended in a venturi shape, as shown by a dotted line in the drawing, the slot 16 is generally linearly extended with an extension angle $\theta \leq 40°$ for simplification. The perspective view of FIG. 6 shows the state of the width and thickness of the slot 16.

According to the present invention, by supplying the monomer solution having a continuous concentration gradient and the polymerizing reaction initiator solution to the coating head as the gel forming solution for electrophoresis while mixing the former solution and the latter solution with each other, it is possible to stably produce coating membrane having a distinct concentration gradient, which could not be accomplished in the prior art, because the gel forming solutions can be supplied to the coating head, for example, by the agitating force of the static mixer and the self-advancing forces of the liquids themselves without being mixed with each other. Further, it is possible to produce coating membrane with comparatively improved productivity in comparison with the conventional method.

Further, according to the present invention, the flow of the coating liquid from the supply inlet to the slot opening is continuously extended in width and continuously reduced in thickness corresponding to the extension in width in order to avoid sudden extension/reduction of the flow. To this end, specifically, (1) the edge lines of the liquid flow path are extended continuously, for example, in the manner of a venturi tube so that the formation of vortices (stagnation) is prevented at the edge lines of the liquid flow path, (2) the thickness of the liquid flow path is reduced corresponding to the extension of the width so that the flow resistance is made uniform over the entire flow path, and (3) the angle $\theta$ of extension in width and the angle $\alpha$ of reduction in thickness are limited, for example, so as to be $\theta \leq 40°$ and $\alpha \leq 0.35°$ when the liquid flow is extended in the direction of width, so that vortices and partial stagnation by the vortices are prevented in the liquid flow.

Further, the reason why no cavity is used is to prevent the generation of vortices, which might otherwise occur if a cavity were provided, at various portions of the reduced portion of the liquid flow when the liquid flows out of the cavity into the slot of the coating head, which would lead to generation of partial stagnation of the liquid due to the vortices, and generation of foreign matter due to stagnation. Accordingly, it is possible to obtain coating film which is uniform over the entire coating transverse width.

EXAMPLES OF THE INVENTION

Description will be made as to an example of the present invention with reference to FIGS. 2 and 3.

As the gel forming solution for electrophoresis:

Low concentration monomer solution (1) was composed of:

| | |
|---|---|
| Agarose | 65 g |
| Urea | 4,200 g |
| Acrylamide | 549 g |
| 1, 3, 5-triacryloyl-hexahydro-S-triazine | 5.7 g |
| Deionized water added up to | 9,000 ml |

High concentration monomer solution (2) was composed of:

| | |
|---|---|
| Agarose | 40 g |
| Urea | 4,200 g |
| Acrylamide | 1,830 g |
| 1, 3, 5-triacryloyl-hexahydro-S-triazine | 19 g |
| Deionized water added up to | 9,000 ml |

Buffer solution (3) was composed of:

| | |
|---|---|
| Trishydroxymethyl amine | 121.14 g |
| Boric acid | 65.4 g |
| Disodium ethylenediamine-tetraacetate | 7.45 g |
| Deionized water added up to | 1,000 ml |

Mixed solution (4) was composed of:

| | |
|---|---|
| Buffer solution (3) | 750 ml |
| 2.9% aqueous solution of polyvinyl pyrrolidone | 800 ml |
| 25% N,N,N',N'-tetramethyl-ethylenediamine liquid | 6.7 ml |

The mixed solution (4) was added to 9,000 ml of the low concentration monomer (1) and to 9,000 ml of the high concentration monomer (2) to thereby prepare the low concentration monomer liquid 1 and the high concentration monomer liquid 2 respectively.

Next, as the polymerizing reaction initiator liquid (3): Mixed solution was composed of

| | |
|---|---|
| 2% di-2 ethyl hexyl sulfosuccinate liquid | 100 ml |
| 0.375% aqueous solution of riboflavin phosphate ester | 150 ml |
| 3.75% aqueous solution of ammonium peroxydisulfate | 160 ml |

The three kinds of solutions 1, 2, and 3 were poured into respective tanks.

While keeping the sum of the respective flow rates of the low and high concentration monomer solutions 1 and 2 supplied by the flow gradient liquid supply pumps 4 and 5 at 19 ml/min, the flow-rate ratio was gradually changed so as to change the concentration gradient from low to high, and then from high to low. The polymerizing reaction initiator solution 3 was supplied into the static mixer 7 at a flow rate of 1.46 ml/min by the metering pump 6.

In the static mixer 7, the foregoing three solutions were mixed and agitated by themselves so as to prepare the electrophoresis gel forming solution 12.

The web 13 was coated with the electrophoresis gel forming solution 12 by the coating head 8.

The flow-rate ratio between the low and high concentration monomer solutions 1 and 2 was changed as shown in the diagram (a) in FIG. 3. The concentration of the applied gel medium membrane assumed the state of the diagrams (b) and (c) of FIG. 3.

PET film having a coating width of 18 cm was coated with 150–200 cc/m$^2$ of the gel forming solution for electrophoresis prepared in the manner described above.

EXAMPLE 1:

Coating was carried out using a coating head under the conditions that the angle $\theta$ of extension in width and the angle $\alpha$ of reduction in thickness were $\theta = 40°$ and $\alpha = 0.35°$ in the slot of the coating head measured from its supplying inlet to its slot opening. No faults, such as generation of coating scars, were caused, even when the coating process was continued for as long as eight hours, and products of superior coating quality with uniform thickness over the entire width were obtained.

EXAMPLE 2:

Similarly to the case of Example 1, coating was carried out on PET film using a coating head under the conditions that the angle $\theta$ of extension in width and the angle $\alpha$ of reduction in thickness were $\theta = 45°$ and $\alpha = 0.5°$, with the same coating liquid concentration and the same temperature as those in the case of the Example 1. Coating was successfully performed using the head for as long as three hours; after continuous coating for three hours, the tendency of the thickness of the coating layer formed being thinner towards the both edges than at the center, and of occurrence of the slight coating streaks were observed.

Next, referring to FIG. 7, a modification of the present invention will be described.

Figure 7A:
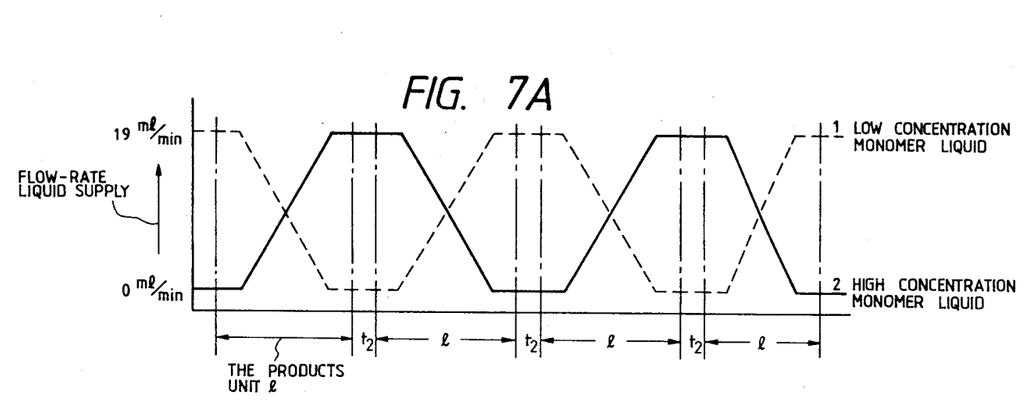
FIG. 7 is a diagram for explaining the relation of the flow-rate ratio between the high and low concentration monomer solutions and the products according to the present invention.

FIG. 7 is a diagram for explaining the relation of the flow-rate ratio between the high and low concentration monomer solutions according to the present invention. The continuous change of the flow-rate ratio is such that, at initiation, the high concentration monomer solution 2 and the low concentration monomer solution 1 are continuously changed in such a manner shown by a solid line and a dotted line, respectively, under the condition that the sum of the flow rates is held constant at 19 ml/min. In the drawing, represents the product unit length of the gradient gel medium membrane for electrophoresis. At the termination of the product unit length 1, the respective flow rates of the high and low concentration monomer solutions 2 and 1 are 19 ml/min and 0 ml/min, so that the membrane component at that time has a high concentration. In the example shown in FIG. 3, the flow rate of the high concentration monomer solution 2 is immediately lowered from 19 ml/min to 0 ml/min, while the flow rate of the low concentration monomer solution 1 is rapidly raised from 0 ml/min to 19 ml/min at the changeover time. In this modification, however, as shown in FIG. 7A, the respective flow rates of the high and low concentration monomer solutions 2 and 1 are left as they are at that time as shown in FIG. 7A, and the next product unit length is formed with the gradient of concentration changing from high to low. Such a change of the flow-rate ratio is repeated.

Figure 7B:
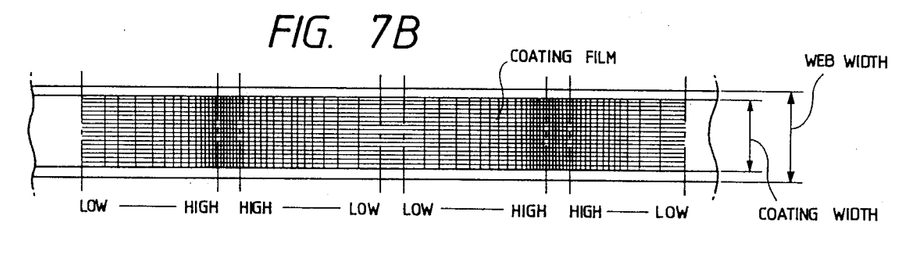
Figure 7C:
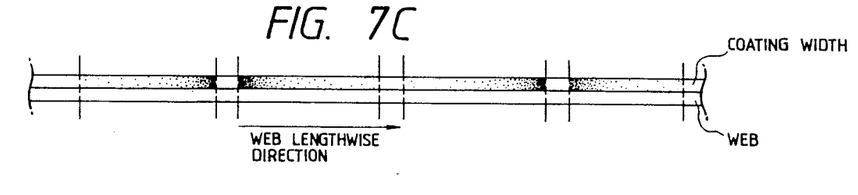

FIG. 7B is a plan view showing gradient gel medium membrane for electrophoresis formed by the concentration ratio of FIG. 7A, and FIG. 7C is a section of FIG. 7B.

A changeover length $t_2$ between adjacent product unit lengths 1 in the drawing is punched as a sample pouring inlet portion where a sample pouring inlet is to be formed by a cover sheet or the like.

In this modification according to the present invention, by producing gradient gel medium membrane for electrophoresis containing urea as a modifier by a method comprising the steps of mixing high and low concentration monomer solutions supplied at respective flow rates, the ratio of which is continuously changed, with a predetermined quantity of polymerizing reaction initiator solution in a static mixer to thereby prepare a gel forming solution for electrophoresis, and coating a continuously moving web with the gel forming solution for electrophoresis, wherein the flow-rate ratio is gradually changed to change the concentration from low to high and then from high to low, the changeover length can be shortened and the solutions can be supplied to a coating head without being mixed with each other. Accordingly, it becomes possible to stably produce coating film with a short change over length $t_2$. Further, it becomes possible to further improve the productivity.

EXAMPLE 3:

Referring to FIGS. 2 and 7 again, an example of the foregoing modification of the present invention will be described. As the gel forming solution for electrophoresis:

Low concentration monomer solution 1 was composed of:

| | |
|---|---|
| Acrylamide | 513 g |
| N, N'-methylene bisacrylamide | 27 g |
| Sodium dodecyl sulfate (pH buffer) | 9 g |
| 1.5M-Tris-hydrochloric acid (pH 8.9) | 2,250 ml |
| Deionized water was added up to | 9,000 ml. |

High concentration monomer solution 2 was composed of:

| | |
|---|---|
| Acrylamide | 1,710 g |
| N, N'-methylene bisacrylamide | 90 g |
| Sodium dodecyl sulfate (pH buffer) | 9 g |
| 1.5M-Tris-hydrochloric acid (pH 8.9) | 2,250 ml |
| Deionized water added up to | 9,000 ml |

(Note) Tris: tris(hydroxymethyl) aminomethane
As the polymerizing reaction initiator solution (3):
Mixed solution was composed of:

| | |
|---|---|
| 2.5% aqueous solution of ammonium peroxydisulfate | 216 ml |
| 25% N,N,N',N'-tetramethyl-ethylenediamine liquid | 2.25 ml |
| 0.375% aqueous solution of sodium riboflavinphosphate ester | 150 ml |

The three kinds of solutions 1, 2, and 3 were poured into respective tanks.

While keeping the sum of the respective flow rates of the low and high concentration monomer solutions 1 and 2 supplied by the flow gradient liquid supply pumps 4 and 5 at 38 ml/min, the flow-rate ratio was gradually changed so as to change the concentration gradient from low to high, and then from high to low. The polymerizing reaction initiator solution 3 was supplied to the static mixer 7 at a flow rate of 1.55 ml/min by the metering pump 6.

In the static mixer 7, the foregoing three solutions were mixed and agitated by themselves so as to prepare the electrophoresis gel forming solution 12.

The web 13 was coated with the electrophoresis gel forming solution 12 by the coating head 8.

The flow-rate ratio between the low and high concentration monomer solutions 1 and 2 was changed as shown in FIG. 7A. The concentration of the applied gel medium membrane assumed the state of FIGS. 7B and 7C. According to the present invention, a changeover length $t_2 = 0.5$ m for every product unit length $1 = 0.2$ m, so that the productivity could be raised by 50% and the production cost could be reduced remarkably.

To form final products, the medium membrane for electrophoresis are subjected to steps of attaching spacers on the opposite end portions of a web in advance, performing hardening processing after coating, punching a comb as a sample pouring inlet, attaching a cover sheet, cutting the web into product lengths, etc., as disclosed, for example, in U.S. Pat. No. 4,699,680 or European Pat. No. 0163472A. The present invention is not directly concerned with those steps, however.

According to the present invention, in a method for producing gradient gel medium membrane for electrophoresis comprising the steps of supplying a monomer solution having a continuous concentration gradient and a polymerizing reaction initiator solution to a coating head as a gel forming solution for electrophoresis while mixing the monomer solution and the polymerizing reaction initiator solution with each other using a static mixer or the like before coating, it becomes possible to stably produce gradient gel medium membrane having an accurate concentration gradient with improved reproducibility and good productivity. Further, the coating liquid is applied onto the moving web through the coating head in such a manner so that the flow of the coating liquid extends continuously in the direction of width and is continuously reduced in the direction of thickness along the coating head from its supply inlet to its slot opening, whereby no foreign matter due to stagnation of the coating liquid is produced in the coating head and coating can be carried out uniformly in the direction of width, so that the products are further improved in quality.

Further, by the method of producing gradient gel medium membrane for electrophoresis according to the present invention, the flow-rate ratio is gradually changed so as to change the concentration from low to high and then from high to low, whereby product loss is reduced by half and productivity is raised by about 50%. Further, the products are improved in stability and reproducibility.

What is claimed is:

1. A method for producing a gradient gel medium membrane for electrophoresis in which a monomer solution having a continuous concentration gradient and a polymerizing reaction initiator solution are supplied to a coating head as a gel forming solution for electrophoresis while mixing said monomer solution and said polymerizing reaction initiator solution with each other so as to coat a running web with said gel forming solution, including the step of supplying said coating liquid onto said moving web through said coating head in such a manner that the flow of said coating liquid extends continuously in the width direction and is continuously reduced in the thickness direction along said coating head from a supply inlet thereof to a coating slot thereof, wherein an angle $\alpha$ of reduction in width and an angle $\theta$ of extension of said coating head from said supply inlet thereof to said coating slot thereof are, respectively, $\alpha \leq 0.35°$ and $\theta \leq 40°$, and a flow rate ratio of said gradient of said monomer solution is gradually changed to change the concentration from low to high for a product length and then from high to low for a subsequent product length.

2. The method for producing a gradient gel medium membrane of claim 1, wherein the thickness of coating on said web is in a range of about 50 $\mu$m to about 1.0 mm.

3. The method for producing a gradient gel medium membrane of claim 1, wherein the thickness of coating on said web is in a range of about 200 $\mu$m to about 0.5 mm.

4. The method for producing a gradient gel medium membrane of claim 1, wherein said web is made of a porous material, and the thickness of coating on said web is in a range of about 70 $\mu$m to about 1.0 mm.

* * * * *